United States Patent [19]
Preston et al.

[11] Patent Number: 5,837,532
[45] Date of Patent: Nov. 17, 1998

[54] HERPES SIMPLEX CIRUS TYPE 1 MUTANT

[75] Inventors: Christopher Maurice Preston, Glasgow, United Kingdom; Christopher Ian Ace, Worcester, Mass.

[73] Assignee: British Technology Group Limited

[21] Appl. No.: 435,280

[22] Filed: May 5, 1995

Related U.S. Application Data

[63] Continuation of Ser. No. 112,882, Aug. 27, 1993, abandoned, which is a continuation of Ser. No. 998,703, Dec. 30, 1992, abandoned, which is a continuation of Ser. No. 834,273, Feb. 12, 1992, abandoned.

[30] Foreign Application Priority Data

Aug. 15, 1989 [GB] United Kingdom .................... 8918616

[51] Int. Cl.$^6$ ..................................................... C12N 15/86
[52] U.S. Cl. .................. 435/320.1; 536/23.2; 536/23.72
[58] Field of Search ................................. 735/69.1, 69.8, 735/172.1, 172.3, 91.4, 91.41, 91.42, 320.1, 235.1; 424/93.1, 93.2, 93.6; 536/23.1, 23.2, 23.72

[56] References Cited

U.S. PATENT DOCUMENTS

| | | | |
|---|---|---|---|
| 4,859,587 | 8/1989 | Roizman | 435/69.1 |
| 5,501,979 | 3/1996 | Geller et al. | 435/320.1 |

FOREIGN PATENT DOCUMENTS

| | | |
|---|---|---|
| 0243155 | 10/1987 | European Pat. Off. . |
| 0282330 | 9/1988 | European Pat. Off. . |
| 453242 | 10/1991 | European Pat. Off. . |

OTHER PUBLICATIONS

A.I. Geller and X.O. Breakefield; A Defective HSV–1 Vector Expresses *Escherichia coli* β–Galactosidase in Cultured Peripheral neurons; *Science* (1988).

Breakfield et al., "Herpes Simplex Virus for Gene Delivery to Neurons", The New Biologist, vol. 3, No. 3, 1991, pp. 203–218.

Journal of Virology, vol. 63, No. 5, May 1989, Chris I. Ace et al.: "Construction and Characterization of a Herpes Simplex Virus Type 1 Mutant Unable to Transinduce Immediate–Early Gene Expression", See p. 2260—p. 2269—see the whole document.

Science, vol. 244, Jun. 1989, Theodore Friedmann: "Progress Toward Human Gene Therapy", see p. 1275—p. 1280—p. 1277.

Science, vol. 241, Sep. 1988, Alfred I Geller et al.: "A Defective HSV–1 Vector Express *Escherichia coli* B–Galactosidasein Cultured Peripheral Neurons", see p. 1667—p. 1669—see whole document.

*Primary Examiner*—David Guzo
*Attorney, Agent, or Firm*—Bell, Seltzer, Park & Gibson

[57] ABSTRACT

A herpes simplex virus type I (HSV-1) mutant capable of establishing latent infection in the absence of in vivo viral replication in neuronal cells and of expressing an inserted therapeutic gene, which comprising: (i) a DNA sequence change in the gene coding for Vmw65 protein, such as to substantially remove the transducing properties while retaining its structural role and thereby preventing in vivo replication, the DNA sequence change being achieved by a transition or transversion alteration of 1 to 72 base pairs, an oligonucleotide insert of 3 to 72 base pairs, or a deletion of 3 to 72 base pairs, at a position between amino acids 289 and 412 of the protein; and (ii) a therapeutic gene inserted into a region of the HSV-1 genome which is non-essential for culture of the virus, and a promoter therefor able to express the therapeutic gene in neuronal cells in vivo. The preferred insertion site for the therapeutic gene (e.g. tyrosine hydroxylase gene) is within the thymidine kinase gene of HSV in 1814.

13 Claims, 3 Drawing Sheets

HERPES SIMPLEX CIRUS TYPE 1 MUTANT

This is a continuation of application Ser. No. 08/112,882 filed on 27 Aug. 1993, abandoned, which is a continuation of 07/998,703 filed on 30 Dec. 1992, abandoned, which is a continuation of 07/834,273 filed on 12 Feb. 1992, abandoned.

FIELD OF THE INVENTION

The present invention relates to a mutant of herpes simplex virus type 1 (HSV-1) capable of establishing efficient latent infection in the absence of in vivo viral replication in neuronal cells and of expressing an inserted therapeutic gene. It is particularly useful for the therapy of neurological disease due to or associated with genetic deficiency.

BACKGROUND

A distinguishing feature of herpesvirus infections is the ability to persist in the host for long periods in a nonreplicative or latent state. Herpes simplex virus type 1 (HSV-1) establishes latent infection in human peripheral sensory ganglia, and can reactivate to produce recurrent mucocutaneous lesions in the innervated dermatome (for a review see Baichwal and Sugden, 1988; Hill, 1985; Roizman and Sears, 1987). Operationally, the pathogenesis of herpesvirus infections can be divided into several distinct stages which can be studied individually in experimental animal models: acute viral replication, establishment of latency, maintenance, and reactivation (Hill, 1985; Roizman and Sears. 1987). Following inoculation, HSV-1 replicates at the site of inoculation and is transported to sensory ganglia. Replication at the periphery or in sensory ganglia, measured by viral titers of tissue homogenates, may increase the amount of virus that can establish latent infection. During latent infection, HSV-1 DNA can be detected in infected tissues, but infectious virus can not (Deshmane and Fraser, 1989; Efstathiou et al., 1986: Fraser et al., 1986; Rock and Fraser. 1983). This latent state is often maintained for the life of the host. A variety of stimuli (such as febrile illness and X-ray irradiation) can interrupt the latent stare and cause the reappearance of infectious virus, or reactivation.

Most of the information about acute viral replication and gene expression has been obtained in tissue culture systems. The HSV-1 lytic replication cycle has been described as a coordinated process that involves the temporal regulation of at least three viral gene classes: $\alpha$, $\beta$, $\gamma$ (for a review see Roizman and Sears, 1987). Five immediate early genes (IE. $\alpha$) have been identified that are first expressed in infected cells prior to viral protein synthesis. Two of these genes, ICP4 and ICP27, are essential for viral replication in cell culture (Dixon and Schaffer, 1980: Preston 1979: Sacks et al. 1985). The $\alpha$ genes activate $\beta$ genes, many of which are enzymes involved in nucleotide metabolism, leading in turn to activation of $\gamma$ genes, many of which are structural components of the mature virus particle. Following corneal inoculation, a broad spectrum of HSV-1 genes from the $\alpha$, $\beta$, and $\gamma$ gene classes can be detected by in situ hybridization and Northern blot analysis during the acute phase of viral replication in mouse trigeminal ganglia (Deatly et al., 1987; Spivack and Fraser, 1988a).

There has been recent progress in characterizing HSV-1 gene expression during latent infection. After the first 5–6 days post infection in mice, HSV-1 gene expression in trigeminal ganglia is limited (Spivack and Fraser, 1988a). This correlates with the decline of infectious virus in trigeminal ganglia (Knotts et al., 1974; Steiner et al., 1989). As early as four days post infection, the HSV-1 latency-associated transcripts (LATs; Spivack and Fraser, 1987; Stevens et al., 1987) begin to accumulate in trigeminal ganglia (Spivack and Fraser, 1988a). The LATs are present predominantly in neuronal cell nuclei (Deatly et al. 1987; 1988; Steiner et al., 1988; Stevens et al., 1987; Stroop et al, 1984), and are not extensively polyadenylated (Spivack and Fraser, 1987). These 2.0, 1.5 and 1.45 kb transcripts, are encoded by diploid genes within the repeat regions of the viral genome (Spivack and Fraser, 1987). The detailed structure of these genes and their regulatory elements is still incomplete. The 2.0 kb LAT is detectable at low levels in infected tissue culture cells (Spivack and Fraser. 1987), and appears to be regulated differently than any of the previously defined classes of HSV-1 genes (Spivack and Fraser, 1988b).

The function of the LATs has only recently been examined; genetic analysis indicates that the LATs are not required for the establishment of latent infection (Javier et al., 1988; Steiner et al., 1989), but that they might play a role in the reactivation process (Steiner et al., 1989). Although a variant HSV-1 virus which does not express the LATs establishes latent infection in mouse trigeminal ganglia, it reactivates in explanted ganglia much more slowly than wild-type virus (Steiner et al., 1989). During the reactivation process there is a lag period before the synthesis of viral RNA, DNA, or infectious virus can be detected (Spivack and Fraser. 1988a). The levels of the LATs decline about two fold during this period, even when reactivation is blocked by inhibitors (Spivack and Fraser, 1988a). Presently, there is little information about the switch to lytic or latent HSV-1 gene expression during the initial stages of infection, or from latent to lytic transcriptional programs during the reactivation process. It is likely that both viral and cellular transcription factors are important determinants.

Transcription of the HSV-1 IE genes is not detectable during latency (Deatly et al., 1987; Spivack and Fraser, 1987; Steiner et al., 1988; Stevens et al, 1987). However, in tissue culture, IE gene expression is a prerequisite for viral replication (Dixon and Schaffer, 1980; Preston, 1979; Roizman and Sears, 1987; Sacks et al., 1985). Transcription of the IE genes is transinduced by a virion protein, Vmw65 (trans-inducing factor, or $\alpha$TIF), that is a component of the HSV-1 virion (Batterson and Roizman, 1983; Campbell et al., 1984; O'Hare and Hayward, 1987; Post et al., 1981; Preston et al., 1984). Vmw65 does not bind directly to HSV-1 DNA, but mediates transinduction by association with cellular proteins to form a complex which interacts with the IE regulatory element TAATGARAT (Gerster and Roeder, 1988; McKnight et al., 1987; O'Hare and Goding, 1988; Preston et al., 1988) Since the expression of IE genes is a critical factor in the outcome of HSV-1 infection in tissue culture cells, the presence or absence of functional Vmw65 might be an important determinant of productive and latent infection in vivo (Ace et al., 1989; Roizman and Sears, 1987).

An HSV-1 mutant, in 1814 (Ace et al., 1989), which contains a 12 bp insertion in the coding region of Vmw65, is unable to transinduce IE gene expression, but the altered Vmw65 is incorporated into mature virions. Replication of in 1814 during infection is dependent upon the multiplicity of infection (MOI). The Vmw65 defect is partially overcome by infection at high multiplicities. At high MOI ($10^2$–$10^3$ particles/cell), the expression of ICP0 and ICP27 is significantly reduced, ICP22 slightly reduced, and ICP4 expression is unaffected (Ace et al., 1989). At lower in 1814 MOI (1–10 particles/cell), the expression of HSV-1 thymidine kinase, an indicator β gene is profoundly reduced, suggesting that IE gene expression is insufficient to activate the viral replication cycle (Ace et al., 1989).

SUMMARY OF THE INVENTION

The present invention provides a herpes simplex virus type 1 (HSV-1) mutant capable of establishing latent infection in the absence of in vivo viral replication in neuronal cells and of expressing an inserted therapeutic gene, which comprises (i) a DNA sequence change in the gene coding for Vmw65 protein, such as to substantially remove the transinducing properties whilst retaining its structural role and thereby preventing in vivo replication, the DNA sequence change being achieved by a transition or transversion alteration of 1 to 72 base pairs, an oligonucleotide insert of 3 to 72 base pairs, or a deletion of 3 to 72 base pairs, at a position between amino acids 289 and 412 of the protein; and (ii) a therapeutic gene inserted into a region of the HSV-1 genome which is non-essential for culture of the virus, and a promoter therefor able to express the therapeutic gene in neuronal cells in vivo.

The position and size of the DNA sequence change is important, since it is necessary to substantially remove the transinducing properties of the Vmw65 protein (and thereby prevent in vivo replication of the virus and consequent illness of the patient) whilst at the same time retaining the structural properties of the protein required to successfully assemble the complete virion when the virus is cultured. The mutant virus must be capable of replication under culture conditions so as to be able to produce sufficient quantities of the mutant virus for use, but at the same time the virus should be incapable of replication in vivo. Removal of the transinducing properties of the Vmw65 protein keeps the virus in its latent stage, and prevents progression to active stages of viral replication and expression in vivo. The mutant virus may advantageously be based on the in 1814 phenotype.

It has been surprisingly found that the insertion of a oligonucleotide insert of the size and at the position stated above, prevents in-vivo replication but otherwise does not prevent necessary functions of the virus. Thus, it is found that the mutant virus is translocated into target neuronal cells as efficiently as "wild-type" HSV-1, that the virus remains in the cells and is not eliminated, that the expression of latency—associated transcripts (LAT's) is unaffected, and that the ability of the virus to enter and remain in its latent stage is also unaffected. These properties allow the mutant virus to be successfully used as a vector for introducing and maintaining therapeutic genes specifically into neuronal cells without substantial elimination thereof. This provides a route for therapy of neuronal genetic deficiencies.

The therapeutic gene is generally a gene associated with a neurological genetic deficiency disease i.e. it compensates for an inherited or acquired genetic deficiency. Examples of such therapeutic genes include:

(a) human, rat or mouse tyrosine hydroxylase genes 1,2 or 3, which are relevant to the alleviation of symptoms of Parkinson's disease;

(b) human, rat or mouse nerve growth factor beta subunit, for treatment of Alzheimer's disease and Parkinson's disease;

(c) human, rat or mouse hypoxanthine—guanine phosphoribosyl transferase gene for the treatment of Lesch-Nyan disease; and (d) human beta-hexosaminidase alpha chain gene, for the treatment of Tay-Sachs and Sandhoff's diseases.

(e) human immunodeficiency virus (HIV) nef gene, for the control of neurological symptoms in HIV-positive individuals.

In particular, the in-situ expression of tyrosine hydroxylase by the present HSV-1 mutant may help alleviate the symptoms of Parkinson's disease. Tyrosine hydroxylase is a crucial enzyme in the synthesis of dopamine. Deficiency of dopamine is the major cause of symptoms in Parkinson's disease, and current treatment involving the administration of L-dopa gives only short-lived respite.

The therapeutic gene may be inserted into any region of the viral genome which is non-essential for culture of the virus, i.e. replication of the virus outside the body, particularly in tissue culture.

The insertion of the therapeutic gene could be made in the coding sequences or in flanking control regions of the following HSV genes:

1. The thymidine kinase gene. This is the preferred choice since thymidine kinase is important for pathogenicity of HSV, so that deactivation of its gene may reduce potential pathogenicity of the mutant vector.
2. The deoxyuridine triphosphatase (dUTPase) gene
3. The Uracil-DNA glycosidase gene
4. The US1 gene (otherwise named the IE68 gene)
5. The US2 gene
6. The US3 (otherwise, the protein kinase) gene
7. The US4 (otherwise glycoprotein G) gene
8. The US5 gene
9. The US7 (otherwise glycoprotein I) gene
10. The US8 (otherwise glycoprotein E) gene
11. The US9 gene
12. The US10 gene
13. The US11 gene
14. The US12 (otherwise IE12) gene.
15. The UL55 gene
16. The UL56 gene
17. The gene encoding the latency-associated transcripts
18. The IE110 gene The US nomenclature system is a systematic one. Many of the genes also have common names.

Generally, the promoter should be capable of operation in neuronal cells during the latency stage of HSV-1, for example promoters which control the latency-associated transcripts (LAT's) of HSV-1, or the promoter which controls the neurofilament gene.

Another aspect of the invention relates to the use of the HSV-1 mutant in the therapy of disease, particularly diseases due to or associated with genetic deficiency.

A further aspect of the invention relates to a pharmaceutical composition for administering the mutant virus comprising the virus in a pharmaceutically acceptable carrier.

EXAMPLES

The production of an HSV-1 virus vector in 1814 and evaluation of its ability to infect mice neuronal cells (and remain in the latent stage) without in vivo replication and appearance of the disease will now be described by way of example only.

Thereafter there is described, also by way of example only, the insertion of a gene (the gene coding for β-galactosidase) into the viral vector in 1814 to produce the viral vector in 1850, and expression thereof. The β-galactosidase gene is inserted in order to validate the technology (the presence of the gene being easily detectable). For therapeutic applications, a therapeutic gene would be inserted in an analogous manner, or the β-galactosidase gene in 1850 could be directly replaced by the therapeutic gene.

(I) Production and Evaluation of Viral Vector in 1814

Experimental procedures

Cell culture, virus titration and preparation of virus stocks. Subconfluent monolayers of baby hamster kidney (BHK) 21 clone 13 cells, were infected with HSV-1 strain 17+ (Brown et. al., 1973), insertion mutant in 1814 (Ace et al, 1989) or revertant 1814R (Ace et al., 1989) to produce virus stocks for the infection of mice. The viruses were titered on BHK cells and virus particle concentrations were determined by electron microscopy with latex bead standards. The viral stocks used in PFU/ml (particles/ml) were: 17+—$5 \times 10^8$ ($3.1 \times 10^9$); 1814R—$5 \times 10^8$ ($5.1 \times 10^9$); in 1814—$1.3 \times 10^7$ ($1.2 \times 10^{11}$).

Comparison of viral titers on cells expressing Vmw65. HSV-1 strain 17+, in 1814 and 1814R were titered on MTX5 cells, which are derived from L TK− cells and express Vmw65 (Kmetz et al., 1988). The titers were compared on CV-1, L TK−, and MTX5 cells to determine which cell line would be most sensitive for plaque assay of in 1814 during acute infection and for explant reactivation from trigeminal ganglia. Although the MTX5 cells provided Vmw65 in trans, and did complement in 1814 when compared with L TK− cells, the titers of in 1814 were not greater on MTX5 cells than on CV-1 (data not shown). Moreover, in 1814 did not form distinct plaques on MTX5, which made the determination of viral titers less exact and more difficult than on CV-1. Thus, CV-1 cells were used as indicator cells in most experiments. In order to increase the sensitivity of this assay, ultraviolet-irradiated tsK virus was absorbed to CV-1 cells at 0.1 PFU per cell (based on titer before UV irradiation) and in 1814 from the primary stock as well as trigeminal ganglia homogenates were titered on these cells. This procedure increases the plaque formation ability of in 1814 by 3 log (Ace et al., 1989) so that the particle/PFU ratio similar to that of the wild type virus.

Infection of mice and viral titers during acute infection. Following corneal scarification, 4 to 6 week old female BALB/cBYJ mice (Jackson Laboratories) or BALB/c (Harlan Sprague Dawley) were infected with approximately $10^5$ PFU/eye of 17+, 1814R or in 1814 (Table 1). Starting at day one post infection, mice were sacrificed by cervical dislocation, corneas were swabbed under sterile conditions with cotton tip applicators and the applicators were incubated with CV-1 cells. Trigeminal ganglia and eyes were removed aseptically, homogenized in 1 ml media without serum, and titered for infectious HSV-1 on CV-1 or on MTX5 cells, as described above.

Explant reactivation

A. At a minimum of 4 weeks after infection, latently infected mice were sacrificed, the trigeminal ganglia were removed and incubated with monolayers of CV-1 cells. Mice were from a group infected at $10^5$ PFU/eye with 17+, 1814R or in 1814 or at equal particle number of approximately $10^6$/eye (Table 2). Another infection was done with $10^4$ particles/eye of in 1814. The monolayers were inspected daily for signs of cytopathic effect. Every 4–6 days ganglia were transferred to new monolayers of cells and observed until reactivation occurred, or for a maximum or 35 days. After reactivation the virus containing media were removed and saved for DNA extraction. As a latency control, ganglia which were titered at explant, from mice 5 and 7 weeks after infection, were negative for infectious virus.

B. In order to determine the time at which in 1814 latency was established, trigeminal ganglia were removed at the indicated times post infection from mice infected with in 1814 for explant reactivation and to titer infectious virus in ganglion homogenates. As a control, trigeminal ganglia from mice infected with 17+ were explanted and the monolayer of cells observed daily for cytopathic effect.

Extraction and quantitation of latent viral DNA from trigeminal ganglia. DNA was extracted from trigeminal ganglia, as described previously (Rock and Fraser, 1983). 5 μg from each sample of 3 pairs of trigeminal ganglia were spotted on a nitrocellulose filter, wetted with 6× SSC, baked for 2 hr at 80° C., and hybridized with a nick translated $^{32}$P-labeled HSV-1 (F) virion DNA probe. After washing, the filter was autoradiographed with XAR-5 (Kodak) film and an intensifying screen at −70° C.

DNA extraction from reactivated virus. Individual plaques of reactivated virus were used to infect CV-1 cells and grow viral stocks.

Nucleoprotein associated HSV-1 DNA was prepared from cytoplasmic fraction of infected cells as described by Pignatti et al. (1979). Briefly, infected cells were lysed by 0.25% Triton X-100, 10 mM EDTA, 10 mM tris-HCl, pH 7.9 (final concentration $1.5 \times 10^7$ cell/ml) and incubated at room temperature for 10 min with gentle mixing. NaCl was then added to a final concentration of 0.2M and centrifuged at 100×g at 4° C. for 10 min. The supernatant was incubated with 100 μg/ml proteinase K and 0.2% SDS at 37° C. for 2 hours and DNA was extracted with phenol, phenol-chloroform and chloroform followed by ethanol precipitation. DNA amounts were measured by $A_{260}$.

DNA analysis. DNA was cut with restriction enzyme BamHI, resolved by 0.8% agarose gel electrophoresis. Southern blot transferred to nitrocellulose, hybridized with HSV-1 (F) restriction fragment BamHI F and washed by standard procedures (Rock and Fraser, 1983). The filters were autoradiographed with XAR-5 film at −70° C. with intensifying screens (Du Pont).

Preparation of $^{32}$P-labelled probes. Total HSV-1 DNA was isolated from virions and purified by CsCl gradient centrifugation. The BamHI F restriction, fragment of HSV-1 (strain F) cloned into pBR322 was a generous sift of B. Roizman (Post. et al. 1980). Restriction enzymes were purchased from Boehringer Mannheim Biochemicals and used as recommended by the manufacturer. DNA probes were nick-translated by a standard procedure (Maniatis et. al., 1982). The probes were separated from unincorporated nucleotides by passage through Sephadex G-50 mini spin columns (Boehringer). The specific activities of the probes were at least $8 \times 10^7$ cpm/μg of DNA.

Results

Acute viral replication in eyes and trigeminal ganglia of mice and mortality rates.

A. Corneas and eyes. Following corneal inoculation with the parental virus 17+, or the revertant 1814R, infectious virus was detected in corneal swabs for 5 days post infection (Table 1), while in 1814 was only detected in 5/8 corneal swabs on the first day post-infection and in 3/8 on the second day. Both 17+ and 1814R reached titers of about $10^4$ PFU/eye (FIG. 1), with the peak titers occurring on the third and second days post-infection, respectively. The titers of in 1814 in eye homogenates were approximately $10^2$ PFU on the first day post-infection, and dropped below detection by the third day. To examine the possibility that the infectious in 1814 virus present in eye homogenates was due to remnants of the viral inoculum rather than viral replication, the viral stock used to infect mice was incubated at 37° C. and titered daily. On each of the three days the titer of in 1814 incubated at 37° C. was greater than the titer in eye homogenates of in 1814 infected mice (data not shown). To increase the detection of in 1814, Vmw65 was provided in trans to the indicator cells with an ultraviolet inactivated HSV-1 strain, tsK (Ace et al., 1989), which restores the particle/PFU ratio of in 1814 to that of the wild-type virus. While the in 1814 titer of the stock used to infect mice was increased 1000 fold by tsK. no infectious in 1814 was detected in eye homogenates during days 3–5 post infection.

B. Trigeminal ganglia. The peak of viral replication in the trigeminal ganglia for 17⁺ and 1814R was on the fifth day post-infection, after which viral titers declined until day 11 (FIG. 2). No infectious in 1814 was detectable in trigeminal ganglia throughout this period, when titered on CV-1 (FIG. 2). To increase the sensitivity of the assay, entire trigeminal ganglia homogenates from in 1814 infected mice were incubated with CV-1 cells in 6 well plates without added immunoglobulin. Infectious in 1814 virus was not detected by this procedure. In another set of experiments Vmw65 was provided in trans to the indicator cells by i) using MTX5 cells (constitutively expressing Vmw65, Kmetz et al. 1988), or ii) by prior infection with ultraviolet inactivated tsK virus. No infectious in 1814 was detected in trigeminal ganglia homogenates during days 3–5 post infection by these methods.

C. Mortality. While mortality rates of mice infected with 17⁺ and 1814R were similar and ranged between 35–60% in independent experiments, none of 127 in 1814 infected mice died.

Explant reactivation of latent 17⁺, 1814R and in 1814

A. Mice infected at equal PFU. Reactivation of latent HSV-1 was assayed at 28–37 days post infection by incubating explanted ganglia with monolayers of susceptible cells (CV-1), and inspecting them daily for cytopathic effects. In all mice infected with strain 17⁺ (7 mice, 14/14 ganglia) reactivation was detectable between 5 and 6 days post explant (Table 2). Similarly, in the trigeminal ganglia of mice infected with 1814R reactivation occurred in all animals examined (24/24 ganglia) between days 5 to 9 post-explant. Reactivation of latent in 1814 from trigeminal ganglia was detected in all latently infected mice (19/20 trigeminal ganglia) between 5 to 10 days post-explant. No infectious virus was detectable in latently infected ganglia at explant, as measured by virus titer or ganglionic homogenates.

B. Mice infected at equal particle numbers. Since there was a 3 log difference in particle/PFU ratio between 17⁺ (or 1814R) and in 1814 (Table 2), the in 1814 inoculum of equal PFU contained approximately $10^3$ more particles than 17⁺ or 1814R. We therefore examined the ability of in 1814 to form a latent infection with equal numbers of inoculated particles. In mice infected with $1.45 \times 10^6$ particles ($1.6 \times 10^2$ PFU), reactivation from latent infection was apparent at 6–8 days post-explant in 4/14 trigeminal ganglia. Thus, in 1814 can form latent infection at particle numbers equivalent to those of 17⁺ and 1814R. However, reactivation was not observed from the trigeminal ganglia of 7 mice infected with $1.45 \times 10^4$ particles (1.6 PFU) of in 1814.

Analysis of reactivated viral DNA. To confirm that the insertion in the Vmw65 gene of in 1814 remained unchanged during latent infection, Southern blots were carried out with BamHI digested DNA isolated from reactivated 17⁺, 1814R and in1814, hybridized with nick-translated HSV-1 (strain F) BamHI restriction fragment F, which encodes Vmw65.

The data demonstrate that the 12 bp insertion introduced into Vmw65 of in 1814 was preserved during latency and reactivation. Since the insertion in in 1814 contains a BamHI restriction site (Ace et al., 1989), two BamHI restriction fragments (5 and 3 kb) hybridized with BamHI F in in 1814 and in reactivated isolates from in 1814 infected trigeminal ganglia. A single 8 kb band was present with 17⁺ and 1814R DNA. The profiles of reactivated 17⁺, 1814R and in 1814 were the same as previously described, and identical to the patterns of the viruses used for infection (Ace et al., 1989).

Quantitation of latent viral DNA in mice trigeminal ganglia. Since HSV-1 replication was not detected in trigeminal ganglia during acute infection of in 1814, it was important to determine whether this resulted in reduced amounts of in 1814 DNA in the ganglia during latent infection. Somewhat unexpectedly, the amounts of latent in 1814 DNA were comparable to the amounts present during latent infection of either 17⁺ or 1814R and ranged between dilutions of $10^{-4}$ to $10^{-5}$ (w/w) which correspond to 4 to 0.4 HSV-1 genome equivalents per cell.

When is latency established? Since infectious in 1814 was not detected in mouse trigeminal ganglia, but latent infection was established, in 1814 provided a unique opportunity to determine when latency begins. Operationally, a latently infected tissue is defined by; i) the absence of infectious virus, and ii) the capacity to reactivate infectious virus (for a review see Hill, 1985). Trigeminal ganglia from mice infected with in 1814 were explanted starting at 12 hr post infection. Reactivated virus could be detected in 7/14 ganglia at 24 hr post infection, in 9/10 at 36 hr post infection, in 13/14 at 48 hr post infection and in all explanted ganglia from the third day post infection. The elapsed time before detection of reactivated virus was similar for all explant time points, ranging between 5 to 10 days post-explant, and similar to the time required to detect reactivated virus from trigeminal ganglia explanted at one month post infection. No infectious virus was detectable in any in 1814 trigeminal ganglia homogenates during this time period (see FIG. 2). In contrast, trigeminal ganglia explanted from 17⁺ acutely infected mice contained infectious virus (FIG. 2) and caused cytopathic effect within 2 to 3 days post explant which was faster than reactivation of latent virus from ganglia explanted from latent 17⁺ mice at one month post infection (5–6 days, see above).

TABLE 1

Virus positive corneal swabs following corneal infection*.

| Virus | 17⁺ | 1814R | in1814 |
|---|---|---|---|
| day 1 | 8/8 | 8/8 | 8/8 |
| day 2 | 8/8 | 8/8 | 3/8 |
| day 3 | 8/8 | 7/8 | 0/8 |
| day 4 | 7/8 | 6/8 | 0/8 |
| day 5 | 4/8 | 4/8 | 0/8 |
| day 7 | 0/8 | 0/8 | 0/8 |

*number of virus-positive corneas/total corneas

TABLE 2

Reactivation of latent in1814, 1814R and 17⁺ from mice infected with equal PFU or equal particles.

| Virus | 17⁺ | 1814R | in1814 | in1814 | in1814 |
|---|---|---|---|---|---|
| Inoculum/mouse | | | | | |
| PFU | $1.3 \times 10^5$ | $1.3 \times 10^5$ | $1.3 \times 10^5$ | $1.6 \times 10^2$ | $1.6 \times 10^0$ |
| Particles | $7.8 \times 10^5$ | $1.5 \times 10^6$ | $1.2 \times 10^9$ | $1.5 \times 10^6$ | $1.5 \times 10^4$ |
| Reactivation* | 14/14 | 24/24 | 19/20 | 4/14 | 0/14 |

*Reactivation positive trigeminal ganglia/total number of trigeminal ganglia explanted for co-cultivation.

(II) Production and Expression of in 1850 (containing β-gal gene)

Experimental Procedures

1. Construction of plasmid pTKLATEX

Plasmid pGx166 was obtained from Dr V. G. Preston. It consists of the previously described plasmid pTKl (Wilkie et al, 1979) with an XhoI linker inserted into the unique SstI site in the thymidine kinase (TK) coding sequences. The HindIII site in the vector (pAT153) sequences of pGx166 was removed by cleaving with HindIII, end-filling with T4 DNA polymerase and self ligation, to yield pGX166ΔH3. Plasmid pFJ3 was obtained from Dr F. J. Rixon. It was derived from pCH110 (Pharmacia) by insertion of an XbaI linker into the PvuII site at the upstream extremity of the SV40 enhancer/promoter region. The β-galactosidase gene under the control of the SV40 enhancer/promoter, was excised from pFJ3 as a 4073 bp KbaI/BamHI fragment and cloned between the XbaI and BamHI sites of pUC18(Xho). Plasmid pUC18(Xho) was constructed by insertion of an XhoI linker into the SmaI site of pUC18. The resulting plasmid was named pUC18βgal.

Plasmid pTKEX was constructed from pGX166ΔH3 and pUC18βgal by cloning the XhoI/SalI fragment of pUC18 βgal, containing the β-galactosidase gene, into the XhoI site of pGX166ΔH3 (FIG. 4). A 605 bp PvuI fragment that is known to contain the LAT promoter (Batchelor and O'Hare, 1990) was cloned into the HincII site of pUC18, after first treating with T4 DNA polymerase to create blunt ends, to give pUCLAT. The orientation of the inserted fragment was such that transcription of LAT proceeded away from the HindIII site of pUC18. Plasmid pTKEX was cleaved with XbaI and HindIII and the large fragment isolated, and pUCLAT was cleaved with XbaI and HindIII and the small fragment isolated. These two DNA fragments were ligated together to yield pTKLATEX (FIG. 4).

Construction of the herpes simplex virus mutant in 1850

Plasmid pTKLATEX was cotransfected into BHK cells together with in 1814 DNA, using standard techniques (Preston, 1981). Progeny viruses were subjected to multiple rounds of plaque purification with Southern hybridisation used to screen for viruses containing the pTKLATEX insert at each stage, using methods described previously (Ace et al, 1989). Cell and viral DNA from the amplified progeny of isolated plaques was cleaved with EcoRI, transferred to nylon 'Genescreen plus' membrane, and probed with radio-labelled 2500 bp EcoRI fragment of pGX166ΔH3 (FIG. 4). Viral DNA without insert yielded the 2500 bp band, whereas virus containing the insert yielded two bands, of approximately 5650 bp and 1250 bp (FIG. 4). A virus preparation that contained the pTKLATEX insert but no detectable contamination with in 1814 was named in 1850.

Expression of β-galactosidase

BHK monolayers were infected with 100 particles of in 1850 per cell and incubated at 37°. At 3h and 6h post infection, cells were harvested, cytoplasmic extracts made and β-galactosidase activity measured, as described previously (McKee et al, 1990).

RESULTS

Plasmid pTKEX

To facilitate transfer of genes into the HSV-1 genome, plasmid pTKEX was constructed. The plasmid contains a composite gene, consisting of the prokaryotic β-galactosidase gene controlled by the SV40 enhancer/promoter region, inserted into and disrupting the coding sequences of the HSV-1 thymidine kinase (TK) gene. Plasmid pTKEX is particularly useful for the cloning of promoter sequences or coding sequences, due to the possession of unique restriction endonuclease cleavage sites. Thus, promoter sequences can be introduced between the unique XbaI and HindIII sites, and coding regions can be cloned between the unique HindIII and XhoI sites. Once manipulations of this type have been performed, the resultant plasmids can readily be recombined with HSV-1 DNA or genomic DNA derived from HSV-1, mutants. Recombinants can be identified by the ability to form blue plaques after X-gal overlay, if the β-galactosidase gene is retained. Selection for recombinants may also be achieved by propagation in the presence of compounds, such as 5-bromodeoxyuridine or acyclovir, that are metabolised to inhibitory products by HSV-1 TK. A further means of identifying recombinant viruses containing inserts derived from pTKEX is by restriction of DNA and subsequence 'Southern' blot hybridisation.

Plasmid pTXLATEX

Using the methods described above, the LAT promoter described by Batchelor and O'Hare (1990) was cloned between the XbaI and HindIII sites of pTKEX, replacing the SV40 enhancer/promoter. In pTKLATEX, the LAT promoter controls the expression of β-galactosidase.

HSV-1 mutant in 1850

Plasmid pTKLATEX was recombined with in 1814 DNA, and a virus preparation possessing the inserted DNA was isolated and named in 1850. When in 1850 DNA was cleaved with EcoRI and probed with a radiolabelled 2500 bp EcoRI fragment derived from pGX166ΔH3, hybridisation was noted to fragments of 5650 bp and 1250 bp, but not to the 2500 bp EcoRI fragment present in 1814 DNA. Thus in 1850 is pure, containing no detectable contamination with residual in 1814.

Expression of βgalactosidase by in 1850

When BHK monolayers were infected with in 1850, an increase in β-galactosidase activity was observed (Table 3), demonstrating that the LAT promoter is active in in 1850. Thus the coding sequences for any gene of interest, for example a therapeutic gene, may be introduced into the in 1814 genome under the control of the LAT promoter. This would be achieved by cloning the coding sequences of the therapeutic gene between the HindIII and XhoI sites or pTKLATEX, then recombining the new plasmid DNA with in 1850 DNA. Preliminary selection of recombinants would be achieved by screening for the inability to form blue plaques in the presence of X-gal, an final verification of recombinant structures would be achieved by Southern blot hybridisation.

TABLE 3

| Cell Extract | β-galactosidase activity (arbitrary units per 2 × $10^5$ cells) |
|---|---|
| Mock infected | 0.350 |
| in1850 infected, 3h post infection | 1.135 |
| in1850 infected, 6h post infection | 2.790 |

Derivation of pTKLATEX

Figure 1:
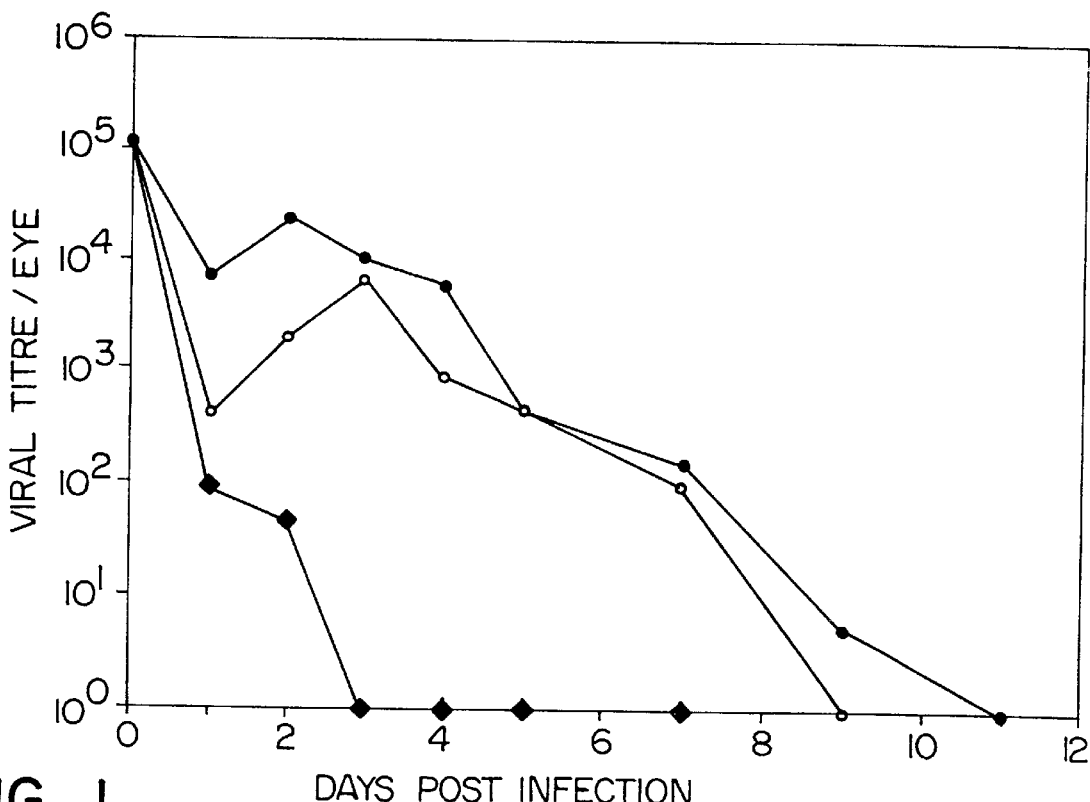
FIG. 1. HSV-1 titers in mouse eyes during acute infection. Each point represents the geometric mean titer from 8 individually titered eyes at the indicated time (days) post infection, from two experiments. The titers are plotted on a logarithmic scale as plaque forming units/eye (PFU/eye). Closed squares—in 1814, open diamonds—17+, closed diamonds—1814R.
Figure 2:
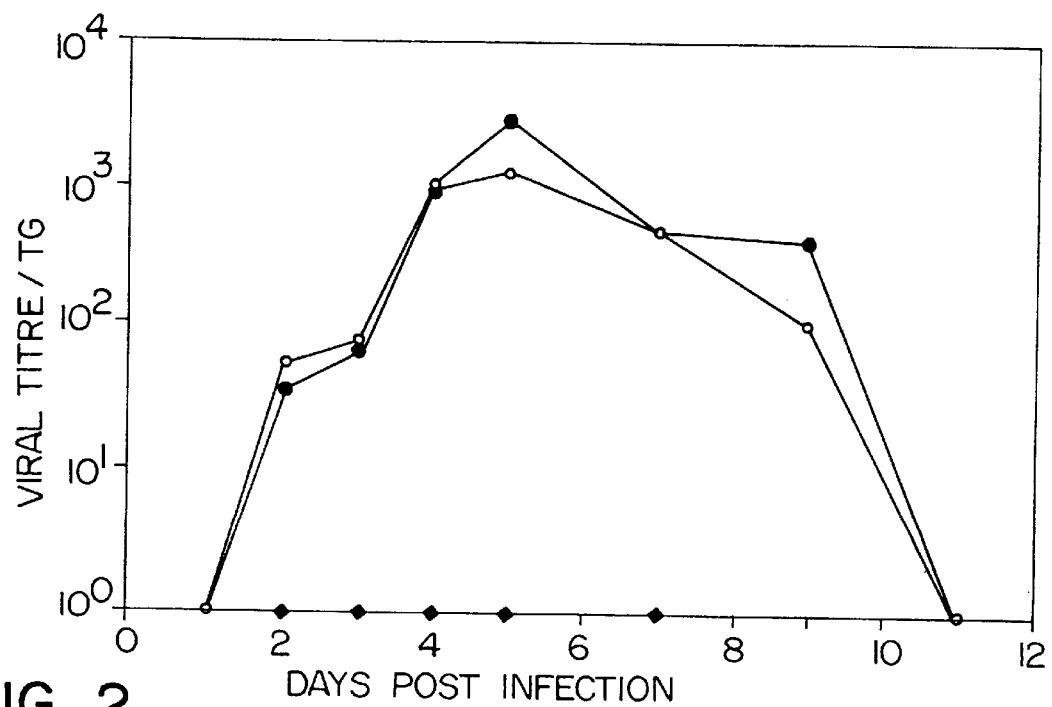
FIG. 2. HSV-1 titers in mouse trigeminal ganglia during acute infection. Each point represents the geometric mean titer from 8 ganglia titered individually at the indicated time (days) post infection, from two experiments. The titers are plotted on a logarithmic scale as plaque forming units/ trigeminal ganglia (PFU/TG). Open diamonds—Strain 17+. Closed diamonds—revertant 1814R. No infectious in 1814 was detected during acute infection (Closed squares).
Figure 3:
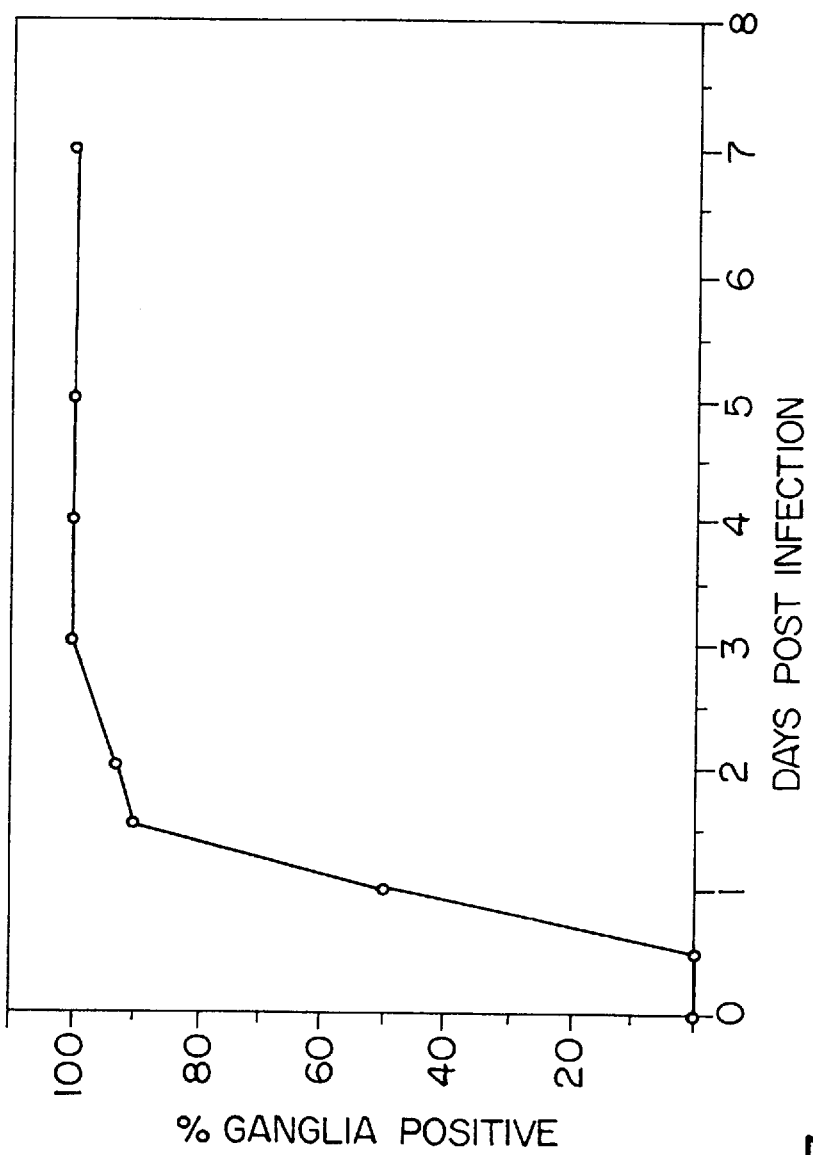
FIG. 3. Time of establishment of HSV-1 latent in 1814 infection in the trigeminal ganglia of mice. A ganglion was scored positive for reactivation when cytopathic effects were detected in the CV-1 monolayer. The numbers are cumulative data from three different experiments: Data is given in percentage of reactivated ganglia at each time point, 10–14 ganglia/point.
Figure 4:
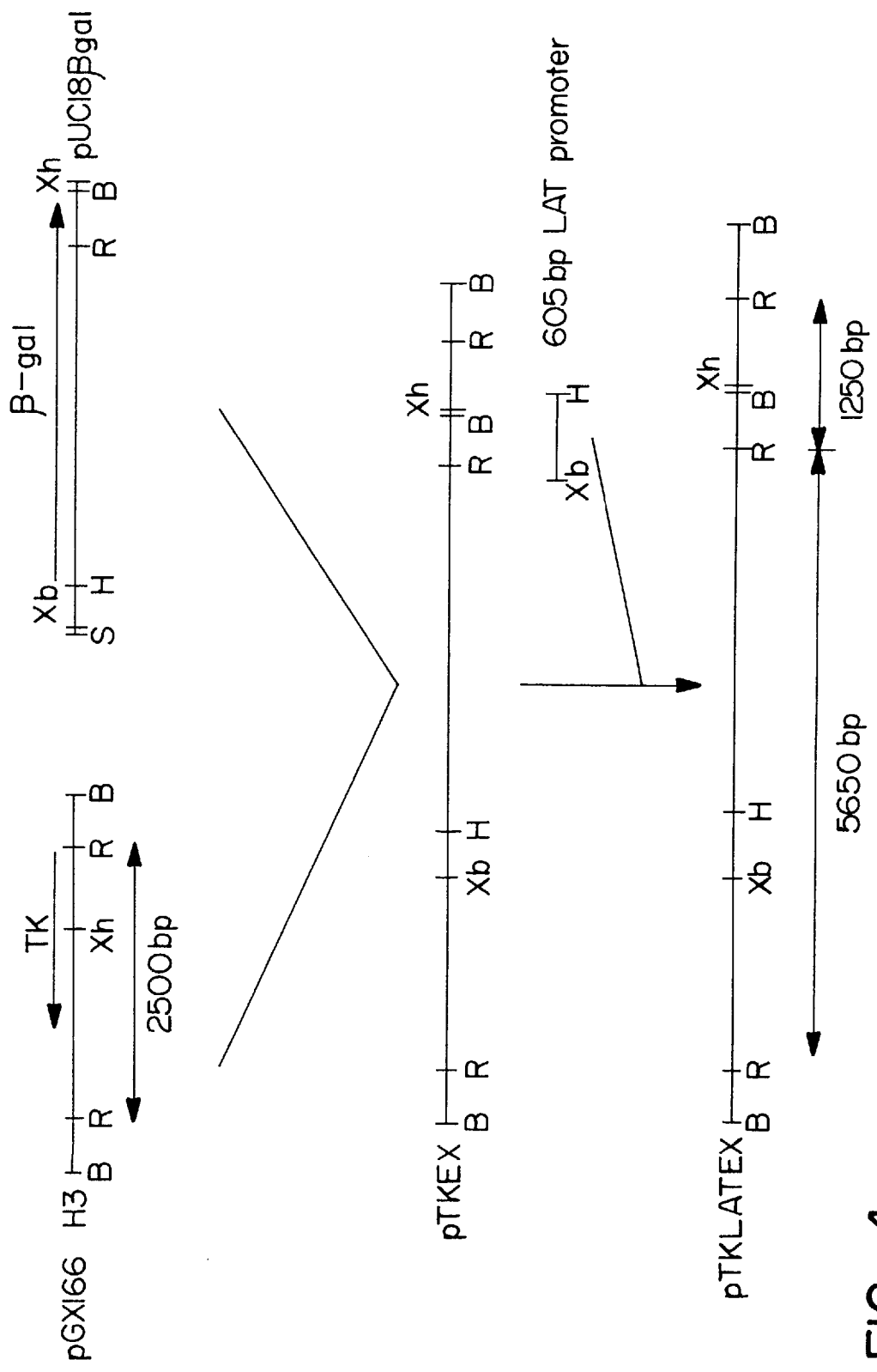
FIG. 4

Abbreviations of restriction endonuclease cleavage sites are: B, BamHI; H, HindIII; R, EcoRI; S, SalI; Xb, XbaI; Xh, XhoI. The 2500 bp EcoRI from pGX166ΔH3, used as a probe for Southern hybridisation, and the 5650 and 1250 bp fragments from pTKLATEX, are shown.

REFERENCES

Ace, C. I., McKee, T. A., Ryan, J. M., Cameron, J. M. and Preston, C. M. (1989). Construction and characterization of a herpes simplex virus type 1 mutant unable to transinduce immediate early gene expression. J. Virol. 63, 2260–2269.

Baichwal, V. R. and Sugden, B. (1988). Latency comes of age for herpesviruses. Cell 52, 787–789.

Batchelor, A. H. and O'Hare, P. (1990). Regulation and cell-type-specific activity of a promoter located upstream of the latency-associated transcript of herpes simplex virus type 1. Journal of Virology 64, 3269–3279.

Batterson, W. and Roizman, B. (1983). Characterization of the herpes simplex virion-associated factor responsible for the induction of α genes. J. Virol. 46, 371–377.

Brown, S. M., Ritchie, D. A. and Subak-Sharpe, J. H. (1973). Genetic studies with herpes simplex virus type 1. The isolation of temperature-sensitive mutants, their arrangement into complementation groups and recombination analysis leading to lineage groups. J. Gen. Virol. 18, 329–346.

Campbell, M. E. M., Palfreyman, J. W. and Preston, C. M. (1984). Identification of herpes simplex virus DNA sequences which encode a trans-acting polypeptide responsible for stimulation of immediate early transcription. J. Mol. Biol. 180, 1–19.

Deatly, A. M., Spivack, J. G., Lavi, E. and Fraser, N. W. (1987). RNA from an immediate early region of the HSV-1 genome is present in the trigeminal ganglia of latently infected mice. Proc. Natl. Acad. Sci. U.S.A. 84, 3204–3208.

Deatly, A. M., Spivack, J. G., Lavi, E., O'Boyle, D. R. and Fraser, N. W. (1988). Latent herpes simplex virus type 1 transcripts in peripheral and central nervous system tissue of mice map to similar regions of the viral genome. J. Virol. 62, 749–756.

Deshmane, S. L. and Fraser, N. W. (1989). During latency, herpes simplex virus type 1 DNA is associated with nucleosomes in a chromatin structure. J. Virol. 63, 943–947.

Dixon, R. A. F. and Schaffer, P. A. (1980). Fine structure mapping and functional analysis of temperature-sensitive mutants in the gene encoding the herpes simplex virus type 1 immediate-early protein VP175. J. Virol. 36, 189–203.

Efestathiou, S., Minson, C., Field, H. J., Anderson, J. R. and Wildly, P. (1986). Detection of herpes simplex virus-specific DNA sequences in latently infected mice and in humans. J. Virol. 57, 446–455.

Fraser, N. W., Deatly, A. M., Mellerick, D. M., Muggeridge, M. I. and Spivack, J. G. (1986). Molecular biology of latent HSV-1. In Human Herpesvirus Infections. C. Lopez and B. Roizman (eds.). Raven Press, New York, pp 39–54.

Gerster, T. and Roeder, R. G. (1988). A herpesvirus trans-activating protein interacts with transcription factor OTF-1 and other cellular proteins. Proc. Natl. Acad. Sci. U.S.A. 85, 6347–6351.

Hill, T. J. (1985). Herpes simplex virus latency. In: The herpesviruses, Vol. 3, B. Roizman (eds.), Plenum Publishing Corp., New York. pp 175–240.

Javier, R. T., Stevens, J. G., Dissette, V. B. and Wagner, E. K. (1988). A herpes simplex virus transcript abundant in latently infected neurons is dispensable for establishment of the latent state. Virology 166, 254–257.

Kmetz, M., Ostrander, M., Schwartz. J. and Draper, K. G. (1988). MTX5: a cell line expressing biologically active HSV-1 Vmw65 protein. Nucl. Acids Res. 16, 4736

Knotts, F. B., Cook, M. L. and Stevens, J. G. (1974). Pathogenesis of herpetic encephalitis in mice after ophthalmic inoculation. J. Infect. Dis. 130, 16–27.

Maniatis, Y., Fritsch, E. F. and Sambrook, J. (1982). Molecular cloning: a laboratory manual. Cold Spring Harbor laboratory, Cold Spring Harbor, New York.

McKee, T. A., Disney, G. H., Everett, R. D. and Preston, C. M. (1990). Control of expression of the varicella-zoster virus major immediate early gene. Journal of General Virology 71, 897–906.

McKnight, J. L. C., Kristie, T. M. and Roizman, B. (1987). Binding of the virion protein mediating α gene induction in herpes simplex virus-infected cells to its cis site required cellular proteins. Proc. Natl. Acad. Sci. U.S.A. 84, 7061–7065.

O'Hare, P. and Goding, C. R. (1988). Herpes simplex virus regulatory elements and the immunoglobulin octamer domain bind a common factor and are both targets for virion transactivation. Cell 52, 435–445.

O'Hare, P. and Hayward, G. S. (1987). Comparison of upstream sequences requirement for positive and negative regulation of a herpes simplex virus immediate early gene by three virus encoded transacting factors. J. Virol. 61, 190–199.

Pignatti. P. F., Meneguzzi, G., Chenciner, N. and Milanesi, G. (1979). Herpes simplex virus DNA isolated from infected cells with a novel procedure. Virology 93, 260–264.

Post, L. E., Conley, A. J., Mocarski, E. S. and Roizman, B. (1980). Cloning of reiterated and nonreiterated herpes simplex virus 1 sequences as BamHI fragments. Proc. Natl. Acad. Sci. U.S.A. 77, 4201–4205.

Post, L. E., Mackem, S. and Roizman, B. (1981). Regulation of α genes of herpes simplex virus: expression of chimeric genes produced by fusion of thymidine kinase with α gene promoters. Cell 24, 555–565.

Preston, C. M. (1979). Control of herpes simplex virus type 1 mRNA synthesis in cells infected with wild-type virus or the temperature-sensitive mutant tsK. J. Virol. 29, 275–284.

Preston, C. M., Cordingley, M. G. and Stow, N. D. (1984). Analysis of DNA sequences which regulate the transcription of a herpes simplex virus immediate early gene. J. Viral. 50, 708–716.

Preston, C. M., Frame, M. C. and Campbell, M. E. M. (1988). A complex formed between cell components and a herpes simplex virus structural polypeptide binds to a viral immediate early gene regulatory DNA sequence. Cell 52, 425–434.

Preston, V. G. (1981). Fine-structure mapping of herpes simplex virux type 1 temperature-sensitive mutations within the short repeat region of the genome. Journal of Virology 39, 150–161.

Rock, D. L. and Fraser, N. W. (1983). Detection of HSV-1 genome in the central nervous system of latently infected mice. Nature (London) 302, 523–525.

Roizman, B. and Sears, A. E. (1987). An inquiry into the mechanisms of herpes simplex virus latency. Ann. Rev. Microbiol. 41, 543–571.

Sacks. W. R., Greene, C. D., Aschman, D. P. and Schaffer, P. A. (1985). Herpes simplex virus type 1 ICP27 is an essential regulatory protein. J. Virol. 55, 796–805.

Spivack, J. G. and Fraser, N. W. (1987). Detection of herpes simplex type 1 transcripts during latent infection in mice. J. Virol. 61, 3841–3847.

Spivack, J. G. and Fraser, N. W. (1988a). Expression of herpes simplex virus type 1 latency-associated transcripts in the trigeminal ganglia of mice during acute infection and reactivation of latent infection. J. Virol. 62, 1479–1485.

Spivack, J. G. and Fraser, N. W. (1988b). Expression of herpes simplex type 1 (HSV-1) latency-associated transcripts and transcripts affected by the deletion in avirulent mutant HFEM: Evidence for a new class of HSV-1 genes. J. Virol. 62, 3281–3287.

Steiner, I., Spivack, J. G., Lirrete, R. P., Brown, S. M., MacLean, A. R., Subak-Sharpe, J. and Fraser, N. W. (1989). Herpes simplex virus type 1 latency-associated transcripts are evidently not essential for latent infection. The EMBO J. 8, 505–511.

Steiner, I., Spivack, J. G., O'Boyle, D. R., Lavi, E. and Fraser, N. W. (1988). Latent herpes simplex virus type 1 transcription in human trigeminal ganglia J. Virol. 62, 3493–3496.

Stevens, J. G., Wagner, E. K., Devi-Rao, G. B., Cook, M. L. and Feldman, L. T. (1987). RNA complementary to a herpesvirus alpha gene mRNA is prominent in latently infected neurons. Science 235, 1056–1059.

Stroop, W. G., Rock, D. L. and Fraser, N. W. (1984). Localization of herpes simplex virus in the trigeminal and olfactory systems of the mouse central nervous system during acute and latent infections by in situ hybridization. Lab. Invest. 51, 27–38.

Wilkie, N. M., Clements, J. B., Boll, W., Mantei, W., Lonsdale, D. and Weissmann, C. (1979). Hybrid plasmids containing an active thymidine kinase gene of herpes simplex virus 1. Nucleic Acids Research 7, 859–877.

We claim:

1. A viral expression vector comprising
   (i) a herpes simplex virus type 1 with a DNA sequence change in the gene coding for Vmw65 protein, the DNA sequence change being a transition or transversion alteration of 1 to 72 base pairs or a deletion of 3 to 72 base pairs or an insertion of an oligonucleotide sequence, said sequence change at a position within said gene coding for said protein between amino acids 289 and 412 of the protein; and
   (ii) a heterologous gene inserted into a region of the HSV-1 genome which is nonessential for culture of the virus, and a promoter therefor which expresses said heterologous gene in neuronal cells.

2. The viral expression vector according to claim 1, wherein the DNA sequence change is achieved by insertion of an oligonucleotide sequence.

3. The viral expression vector according to claim 1, wherein said heterologous gene is a beta galactosidase gene.

4. The viral expression vector according to claim 1, wherein said heterologous gene is inserted in the coding sequence or in the flanking control region of the thymidine kinase gene.

5. The viral expression vector according to claim 1, wherein said heterologous gene is inserted in the coding sequence or in a flanking control region of an HSV gene selected from the group consisting of deoxyuridine triphosphatase gene, uracil-DNA glycosidase gene, US1 gene, US2 gene, US3 gene, US4 gene, US5 gene, US7 gene, US8 gene, US9 gene, US10 gene, US11 gene, US12 gene, UL55 gene, UL56 gene, the gene encoding the latency-associated transcripts, and the IE 110 gene.

6. The viral expression vector according to claim 1, wherein the promoter for said heterologous gene is a promoter controlling production of the latency-associated transcripts.

7. The viral expression vector according to claim 1, wherein the promoter for said heterologous gene is a promoter which controls the HSV neurofilament gene.

8. The viral expression vector according to claim 1 which is in in1850.

9. The viral expression vector according to claim 2, wherein said heterologous gene is inserted into in1814 viral vector.

10. HSV-1 expression vector in1850, said vector containing a heterologous beta-galactosidase gene under the control of the SV40 promoter.

11. The HSV-1 expression vector according to claim 10, wherein said beta-galactosidase gene has been replaced with a different heterologous gene.

12. An HSV-1 viral vector comprising HSV-1 viral vector in1814 and a heterologous gene inserted into a region of the HSV-1 genome which is nonessential for culture of the virus, and a promoter therefor which expresses said heterologous gene in neuronal cells.

13. Plasmid pTKLATEX, or plasmid pTKEX.

* * * * *

UNITED STATES PATENT AND TRADEMARK OFFICE
CERTIFICATE OF CORRECTION

PATENT NO. : 5,837,532

DATED : November 17, 1998

INVENTOR(S) : Preston et al.

It is certified that error appears in the above-identified patent and that said Letters Patent is hereby corrected as shown below:

Title page, item [54] and Column 1:
In the title, "CIRUS" should read --VIRUS--.

Title page, Item [73], "British Technology Group Limited" should read --British Technology Group Limited, London, England--.

In the Foreign Application Priority Data, insert:
   --August 14, 1990   PCT   PCT/GB90/01276--.

In the References Cited, OTHER PUBLICATIONS, line 4, "Breakfield" should read --Breakefield--.

Column 14, line 37, after "is" cancel one occurrence of "in".

Signed and Sealed this

Ninth Day of January, 2001

*Attest:*

Q. TODD DICKINSON

*Attesting Officer*    *Commissioner of Patents and Trademarks*